United States Patent [19]

Djordjevic et al.

[11] Patent Number: 4,507,969
[45] Date of Patent: Apr. 2, 1985

[54] ULTRASONIC LIQUID JET PROBE

[75] Inventors: Borislav B. Djordjevic, Columbia; Stephen C. Traugott, Glen Arm, both of Md.

[73] Assignee: Martin Marietta Corporation, Bethesda, Md.

[21] Appl. No.: 475,583

[22] Filed: Mar. 15, 1983

[51] Int. Cl.³ .......................................... G01N 29/04
[52] U.S. Cl. ...................................... 73/644
[58] Field of Search ........... 73/644; 310/328, 334–336

[56] References Cited

U.S. PATENT DOCUMENTS

| | | | |
|---|---|---|---|
| 3,255,626 | 6/1966 | Van Der Veer | 73/644 |
| 3,431,440 | 3/1969 | Osgood | 73/644 |
| 3,485,088 | 12/1969 | O'Connor | 73/644 |
| 3,555,891 | 1/1971 | Lewis | 73/644 |
| 3,672,211 | 6/1972 | Hatch | 73/644 |
| 3,745,833 | 7/1973 | Armstrong | 73/644 |
| 3,908,445 | 9/1975 | Verdon et al. | 73/644 |
| 4,403,510 | 9/1983 | de Walle et al. | 73/644 |

Primary Examiner—Stephen A. Kreitman
Attorney, Agent, or Firm—Patrick M. Hogan; James B. Eisel; Gay Chin

[57] ABSTRACT

An ultrasonic liquid jet probe for coupling ultrasonic waves with a structure. The probe includes an ultrasonic transducer for emitting or receiving ultrasonic waves, a housing disposed about the transducer and in fluid communication with a source of liquid under pressure, and a nozzle for shaping the flow of liquid into a round jet column and guiding the ultrasonic waves between the transducer and the liquid jet column. The interior of the housing includes first and second chambers fluidly connected by elongated conduits to impart a substantially laminar flow to the liquid flowing into the nozzle which promotes the stability of the liquid jet column discharged from the nozzle.

8 Claims, 5 Drawing Figures

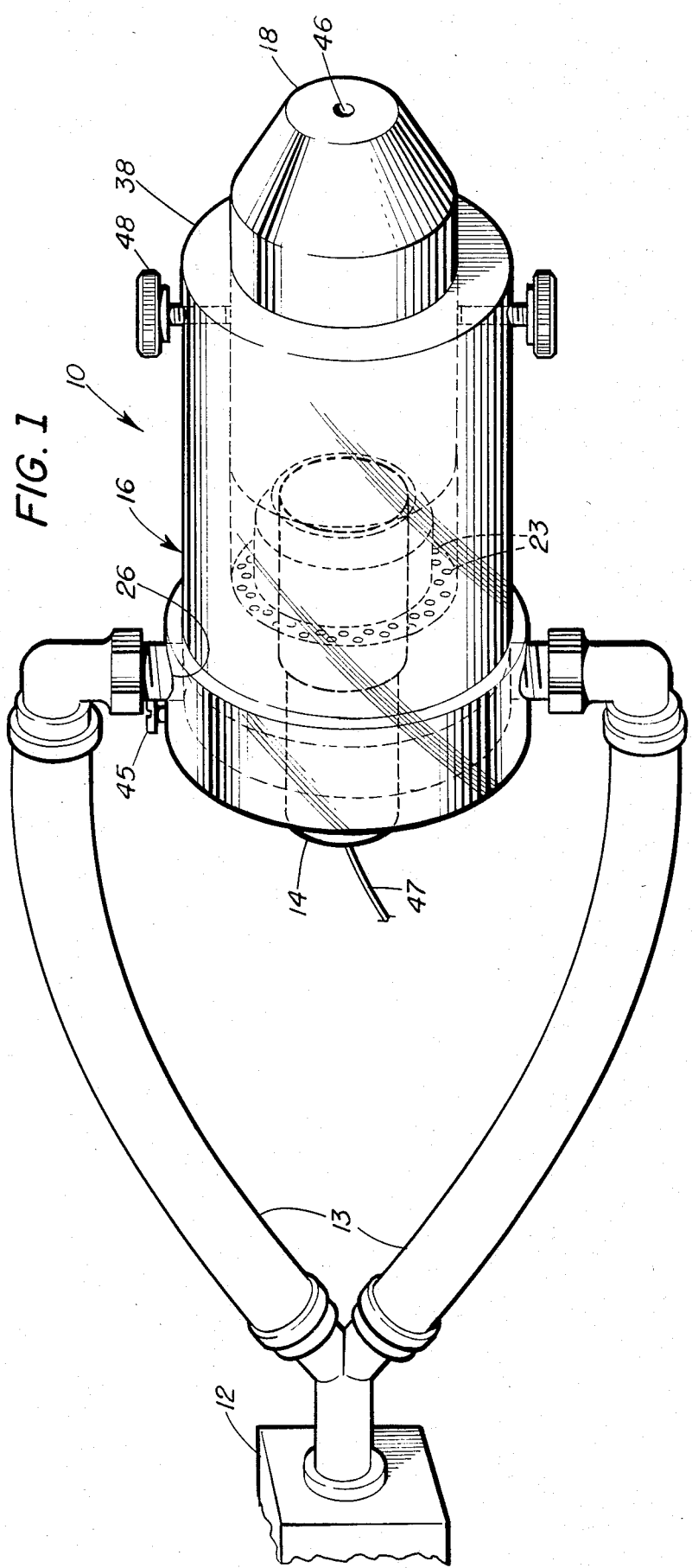
FIG. 1
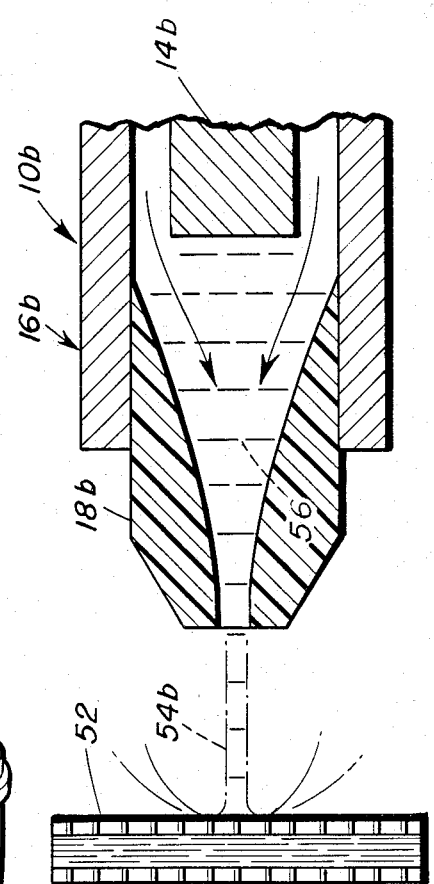
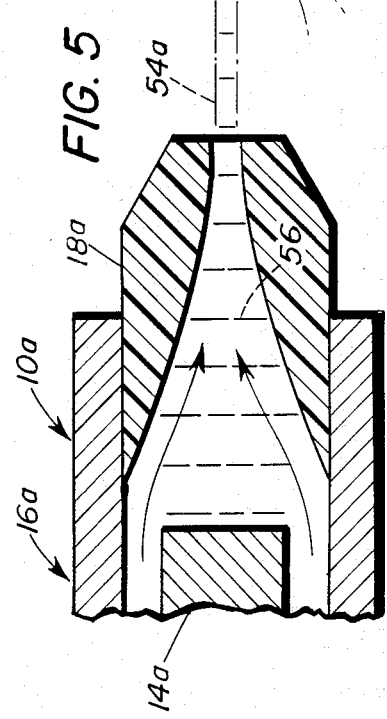
FIG. 5

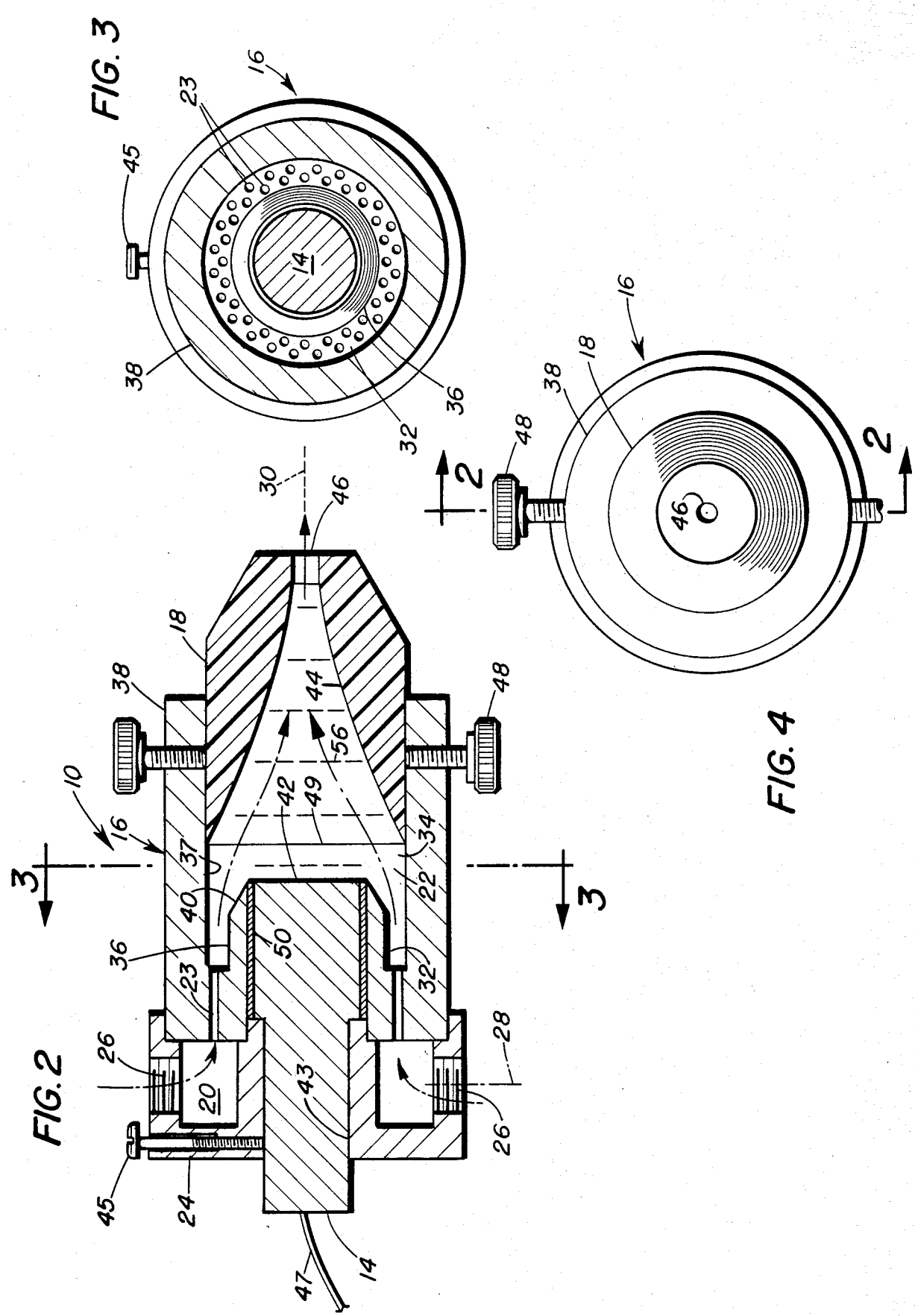

ULTRASONIC LIQUID JET PROBE

BACKGROUND OF THE INVENTION

1. Field of the Invention

This invention relates to test probes for non-destructive evaluation and testing and particularly to a new and improved ultrasonic liquid jet probe which is configured for discharging a stable, uniform liquid jet column and for coupling unmodified ultrasonic waves with a structure.

2. Description of the Prior Art

Ultrasonic waves are often employed in the non-destructive testing of materials and structures, particularly to locate inhomogeneities and defects within the structures or to assess structural integrity and material properties. In one presently utilized method of nondestructive testing, a transducer emits ultrasonic waves which are coupled with the structure being tested by a liquid jet column discharged from a probe. In a particular arrangement, known as the pulse echo mode, the ultrasonic waves are reflected back to the same transducer via the liquid jet column. In a more common arrangement, known as the through transmission mode, the waves pass through the structure and are carried to a receiving transducer by another liquid jet column. In either case, the transducer then converts the waves into electrical signals which are appropriately processed.

Attenuation and spurious reflections of the ultrasonic wave signal, however, reduces the accuracy and reliability of any such liquid jet probe system, but particularly of systems based on the pulse echo mode, that mode being advantageous for reasons of greater compactness and simplicity and because it does not require access to both sides of the test material. Causes of the ultrasonic wave signal degradation include instability and gravitational droop of the liquid jet column and wave reflections within the probe housing.

Instability of the liquid jet column results in a corrugated, asymmetric column surface or turbulence within the column causing not only reflections which tend to mask the true ultrasonic waves, but also a variable and unpredictable amplitude and wave-form of the transmitted ultrasonic signal.

Droop of a nonvertically-oriented liquid jet column occurs when the end of the column curves downwardly due to gravity. The downward displacement of the column is inversely proportional to the flow velocity of the liquid in the column. To avoid signal degradation, it is required that the waves travel essentially undeflected in a straight line and often normally incident to the surface of the test structure. Therefore, in many prior art arrangements in which the liquid jet column is discharged at low flow velocities, the probe must be spaced close to the test surface so as to avoid droop. Although increasing the velocity of the liquid jet column would decrease droop, the higher velocity tends to also create flow irregularities within the column which, as was described above, interferes with the ultrasonic wave signal. It may also be desirable to induce relative motion between the test piece and the probe in order to evaluate large areas of the test piece. If, in available systems which require that the probe be spaced closely to the test piece to avoid droop, the surface of the test piece is of a complex geometric form, elaborate arrangements may be required to enable the probe to follow the surface contour and to avoid ultrasonic signal degradation due to probe orientation.

In many existing probes, the configuration of internal flow passages results in flow instabilities, eddies, unsteadiness and turbulence. These undesirable flow disturbances and irregularities, as well as the materials from which existing probes are fabricated, lead to improper shaping of the ultrasonic wave-form and internal wave reflections as the ultrasonic waves pass through the probe. Such reflections have inhibited attempts to develop workable systems operating in the pulse echo mode where the internal reflections interfere with the true wave reflections from the structure being tested.

In view of the above mentioned problems, it is therefore an object of the present invention to improve the wave coupling performance of ultrasonic liquid jet probes by configuring the probe to discharge a uniform, stable liquid jet column.

Another object of the present invention is to permit an increase in the distance between the probe and the test structure by decreasing the gravitational droop of the liquid jet column.

Another object of the present invention is to provide a probe in which ultrasonic performance is independent of probe orientation.

Yet another object of the present invention is to properly guide ultrasonic waves to the water jet column and to reduce ultrasonic wave interference by reducing internal wave reflections within the probe housing.

Still another object of the present invention is to provide an ultrasonic liquid jet probe of such improved sensitivity and accuracy and low amplitude noise that it can be used in either a through transmission or a pulse echo mode.

SUMMARY OF THE INVENTION

The present invention, in accordance with one embodiment thereof, comprises an ultrasonic liquid jet probe for coupling transducer-emitted ultrasonic waves with a structure. The probe includes a housing disposed about the transducer which comprises inlet means for receiving liquid under pressure from a source thereof, means for imparting a substantially laminar flow to the liquid flowing through the housing, and nozzle means configured for receiving the liquid flowing through the housing and shaping the flow into a liquid jet column to be discharged from the nozzle means and configured and disposed relative to the transducer for guiding the ultrasonic waves between the transducer and the liquid jet column.

In a particular embodiment of the invention, the means for imparting a substantially laminar flow to the liquid comprises the configuration of the interior of the housing including an annular first chamber and a second chamber having an annular chamber section and a cylindrical chamber section. A plurality of circumferentially spaced conduits extend between the first and second chambers and are aligned parallel to the liquid jet column, elongated sufficiently and of sufficient number to promote the laminar flow of liquid. The nozzle means preferably comprises a replaceable nozzle fabricated of a sound attenuating material.

BRIEF DESCRIPTION OF THE DRAWING

This invention will be better understood from the following description taken in conjunction with the accompanying drawing, wherein:

FIG. 1 is a perspective view of the ultrasonic liquid jet probe of the present invention.

FIG. 2 is a cross-sectional view of the probe taken along lines 2—2 of FIG. 4.

FIG. 3 is a cross-sectional view of the probe taken along lines 3—3 of FIG. 2.

FIG. 4 is a front view of the probe showing the nozzle orifice.

FIG. 5 is a cross sectional, partially broken view of a test arrangement employing two probes, one emitting and one receiving ultrasonic waves.

DESCRIPTION OF THE PREFERRED EMBODIMENT

Turning now to a consideration of the drawing, and in particular to FIG. 1, there is shown an ultrasonic liquid jet probe 10 of the present invention. The probe 10 is employed to couple ultrasonic waves with a structure, such as to test the interior of the structure for inhomogeneities and defects.

The probe 10 is configured for receiving liquid under pressure from a source 12 thereof through appropriate delivery tubing 13, and is further configured for supporting an ultrasonic transducer 14 which emits or receives ultrasonic waves. The probe 10 comprises a housing 16 disposed about the transducer 14 and in fluid communication with the source 12 of liquid, and nozzle means, such as the nozzle 18, either integral with or preferably attached to the housing 16. The nozzle 18 is configured to shape the flow of liquid received from the housing 16 into a liquid jet column to be discharged from the nozzle 18 and is configured and disposed relative to the transducer 14 to guide the ultrasonic waves between the transducer 14 and the liquid jet column.

Turning now to FIG. 2, there is shown a cross-sectional view of the probe 10. The housing 16 comprises means for imparting a smooth, regular and substantially laminar flow to the liquid, which could be water or any other desired liquid, flowing through it. Such a laminar, or non-turbulent, flow contributes to a uniform and stable liquid jet column. More specifically, the interior of the housing 16 comprises a first chamber 20 and a second chamber 22, the chambers being fluidly connected by a plurality of circumferentially spaced conduits 23. The first chamber 20 is annular and is disposed near the upstream portion 24 of the housing 16 to receive liquid from the source thereof. The housing 16 includes inlet means comprising two or more inlet ducts 26 which are spaced symmetrically about the housing for conveying the liquid from its source to the first chamber 20. Preferably, each of the inlet ducts 26 is aligned such that its central axis, depicted by the dashed line 28, is substantially normal to the alignment of the conduits 23. This alignment and the symmetrical spacing of the inlet ducts 26, as well as the common source 12 of liquid and the uniform sized tubing 13 (shown in FIG. 1), enhance a uniform distribution of the liquid within the first chamber 20. The uniform distribution of the liquid results in a substantially even distribution of the liquid flow among all of the conduits 23 and thus contributes to the stability of the liquid jet column which is discharged from the nozzle 18.

The conduits 23, which convey the liquid from the first chamber 20 to the second chamber 22, are preferably aligned parallel to the liquid jet column, that is, parallel to the longitudinal axis, depicted by the dashed line 30, of the nozzle 18 and are elongated relative to their diameter. The alignment and elongation of each conduit 23 is sufficient to force the liquid flowing therethrough to travel in a relatively straight path, and thus the conduits promote the smooth and substantially laminar flow of the liquid in the second chamber 22. Turning to FIG. 3, the number, arrangement, length and diameter of the conduits 23 which will best promote the substantially laminar flow of liquid are determined by such factors as the pressure of the liquid entering the probe 10 and the distance between the probe and the structure against which the liquid jet column will impinge. Thus, the conduit arrangement shown in FIG. 3 is presented as an example only. It is desirable, however, that the ratio of inertia to viscous shear forces in the liquid within each of the conduits 23 be low. This ratio is universally known as the Reynolds number. Based on experiments conducted in the development of the present invention, the Reynolds number of the flow of liquid through the conduits 23 should remain below approximately 1,000. For a given liquid viscosity, specific weight and flow rate into the conduits 23, the desired Reynolds number can be achieved by establishing a specific diameter for the conduits 23, Reynolds number being directly proportional to conduit diameter. Flow of a Reynolds number below 1,000 through the conduits 23 will promote smooth and substantially laminar flow throughout the rest of the housing 16.

As is seen in FIG. 2, the second chamber 22 is disposed downstream of the first chamber 20 and comprises an upstream annular chamber section 32 and a downstream cylindrical chamber section 34. The radially inner boundary of the annular chamber section 32 is defined by a tubular extension 36 of the housing 16 while the radially outer boundaries of both the annular and cylindrical chamber sections 32 and 34 are defined by the inner surface 37 of the housing wall 38. It should be noted that FIG. 2 shows the housing 16 as comprising two parts, the upstream portion 24 and the housing wall 38, joined together. Such a configuration facilitates fabrication of the chambers and conduits in the housing interior. Alternatively, if desired, the housing 16 could be fabricated as an integral piece or it could comprise three or more parts joined together.

Preferably, the downstream portion 40 of the tubular extension 36 is beveled radially inwardly for modifying the direction of flow of the liquid as it flows from the annular chamber section 32 to the cylindrical chamber section 34.

The interior of the tubular extension 36 of the housing 16 is sized for receiving and supporting the emitting-/receiving end 42 of the transducer 14. The housing 16 is preferably configured for permitting the entire transducer 14 to be easily replaceable and thus includes a cavity 43 radially inward of the annular first chamber 20, aligned with the center of the interior of the tubular extension 36 and sized and shaped for receiving the rear portion of the transducer 14. The transducer 14 can then be easily replaced by removing the nozzle 18, as will be explained shortly, and sliding the transducer out through the second chamber 22. The housing 16 also includes means for locking the transducer in place, such as the set screw 45. This arrangement also permits the rear portion of the transducer to extend from the housing 16 and simplifies electrical connections, such as the wire 47, between the transducer and other monitoring equipment. Depending upon the use for which the probe 10 will be employed, the transducer 14 will be of the type which either transmits or receives ultrasonic waves or may be of the pulse echo type which both transmits and receives the waves. Also, depending upon its application, the transducer can be either of the focusing or of the non-focusing type.

The nozzle 18 is attached with the housing 16 downstream of the transducer 14 and is aligned with the transducer. Additionally, since the conduits 23 are disposed upstream of the emitting/receiving end 42 of the transducer 14, there are no obstructions between the transducer and the nozzle 18. The nozzle 18 is configured for receiving the liquid flowing from the second chamber 22 of the housing 16 and shaping the flow of the liquid into a liquid jet column to be discharged from the nozzle and for guiding the ultrasonic waves between the transducer 14 and the liquid jet column. Moreover, the shape and location relative to the transducer emitting/receiving end 42 of the nozzle entrance section 49 are such that the entrance section 49 remains outside of the ultrasonic beam thereby avoiding undesirable ultrasonic interaction at that location. A liquid jet column having a round cross sectional shape is preferable to one with a non-round shape because the round shape minimizes wave reflections and distortions of the ultrasonic waves traveling along the jet column. Thus, the inner wall 44 of the nozzle 18 has a shape which guides the smooth and regular laminar flow of liquid from the second chamber 22 into a round liquid jet column with minimum wave-form distortion, the jet column being discharged from the nozzle through the round orifice 46, best seen in FIG. 4, the diameter of the orifice 46 determining the diameter of the liquid jet column. The cross sectional area of the nozzle orifice 46 should, however, be smaller than the combined cross sectional areas of the inlet ducts 26 and also smaller than the combined cross sectional areas of the conduits 23 in order to prevent flow separation and irregularities within the probe 10, which might cause turbulence, and yet to maintain the velocity of the liquid jet column as it is discharged from the nozzle high enough so as to maintain an adequate distance along the jet column free of significant gravitational droop.

The curvature of the nozzle inner wall 44 is determined by factors such as the desired diameter of the liquid jet column and the pressure of the liquid flowing through the probe 10. However, in selecting the nozzle wall curvature, it should also be considered that, for a given liquid pressure and jet column diameter, if the nozzle is short and the wall curvature is high, the stability of the flow of liquid may be compromised, while if the nozzle is long and the wall curvature is low, existing internal liquid disturbances may be amplified, creating an unstable jet column. Thus, to allow flexibility under varying conditions and liquid jet column size requirements while maintaining a stable jet column, it is preferable that the nozzle 18 be replaceable with nozzles having different wall curvatures and orifice sizes. The configuration of FIG. 2 is one example of an arrangement permitting nozzle replacement. The outer surface of the nozzle 18 is shaped and sized such that it closely matches the shape and dimension of the second chamber 22 into which the nozzle is received, the nozzle 18 can thereby slide in or out of the housing 16. The housing 16 includes means for locking the nozzle in place, such as the set screws 48.

The regular and substantially laminar flow induced by the interior of the housing 16 together with a properly shaped nozzle 18 provide a liquid jet column which, compared to many prior art probes, is more uniform and of more constant cross section. In addition, the configuration allows higher liquid discharge velocities from the nozzle without causing flow irregularities, resulting in the column extending further from the nozzle 18 before it begins to droop. For example, during testing of the probe of the present invention, a liquid jet column having a minimum length of 1.5 inches (3.8 cm) before droop was able to be maintained without causing flow irregularities or significant degradation of ultrasonic performance. Moreover, it was found during testing that ultrasonic performance was independent of probe orientation even at that distance.

In addition to shaping the flow of liquid into a liquid jet column, the nozzle 18 is also configured with no obstructions or discontinuities to guide the ultrasonic waves between the transducer 14 and the liquid jet column. Thus, the curvature of the nozzle inner wall 44 and the material from which the nozzle 18 is fabricated will promote optimum guidance of the ultrasonic waves. Preferably, the nozzle 18 is fabricated of sound attenuating material, such as, for example, Teflon TM, available from the DuPont Company, which reduces internal wave reflections. Any such internal wave reflections result in degradation of the ultrasonic signal, particularly when the probe 10 is used in a pulse echo mode where the internal wave reflections would interfere with the true wave reflections from a test structure. The nozzle 18 is also preferably disposed sufficiently close to the emitting/receiving end 42 of the transducer 14 so as to provide an obstruction-free ultrasonic path between the transducer 14 and the nozzle 18 such that the ultrasonic waves emitted by the transducer, indicated by the dashed-line segments 56, are guided to the liquid jet column by only the inner wall 44 of the nozzle. That is, the ultrasonic waves strike neither the inner surface 37 of the second chamber 22 nor the interface between the nozzle 18 and the inner surface 37 nor any other obstruction between the transducer 14 and the nozzle 18. Thus, any potential discontinuities on the inner surface 37 or at the interface with the nozzle 18 would not adversely affect the ultrasonic signal. Such an arrangement helps maintain the strength of the ultrasonic signal by minimizing the distance between the transducer 14 and the structure being tested and therefore also results in a more compact and lightweight probe.

Preferably, and as is shown in FIG. 2, the transducer 14 includes a sleeve 50 fabricated of a sound attenuating material disposed between the transducer and the tubular extension 36 of the housing 16. The sleeve 50 helps reduce internal wave reflections by acoustically isolating the transducer 14 from the housing 16 and is particularly important when the transducer is used in a pulse echo mode. The sleeve 50, together with the configuration of the nozzle 18 result in a greatly improved ratio of ultrasonic signal to noise compared to prior art probes.

Air bubbles within the housing 16 can adversely affect probe performance by interfereing with the flow of liquid therethrough. The housing 16 is therefore preferably fabricated of a transparent material so that such bubbles can be seen and eliminated by pointing the probe 10 vertically and allowing the bubbles to escape through the nozzle orifice 46. Alternatively, an air bleed hole (not shown) could be provided on the top surface of the housing 16 to allow the bubbles to escape.

FIG. 5 shows a typical test arrangement employing two probes 10a and 10b to ultrasonically test a structure 52. Within the probe 10a, the housing 16a imparts a smooth and substantially laminar flow to the liquid flowing therethrough while the nozzle 18a shapes the flow into a round liquid jet column 54a which is discharged from the nozzle and which impinges upon a surface of the structure 52 to be tested. A corresponding liquid jet column 54b is discharged from the nozzle 18b of the probe 10b and impinges upon the opposite surface of the structure 52 in alignment with the liquid jet column 54a. Ultrasonic waves, depicted by the dashed-line segments 56, are emitted by the transducer 14a, guided from the transducer to the liquid jet column 54a by the nozzle 18a, and coupled to the structure 52 by the liquid jet column 54a. The ultrasonic waves 56 pass through the structure 52 and are coupled with the receiving transducer 14b by the liquid jet column 54b. The ultrasonic waves 56 entering the probe 10b are guided by the nozzle 18b to the transducer 14b. The transducer 14b converts the ultrasonic waves into electrical signals which are appropriately analyzed for ultrasonic signal changes characteristic of the structure 52.

Of course, FIG. 5 shows but one example of a use for the ultrasonic liquid jet probe 10 of the present invention and the probe 10 can be effectively employed in many additional ways either singly or in combination with other probes. It is to be understood that this invention is not limited to the particular embodiment disclosed and it is intended to cover all modifications coming within the true spirit and scope of this invention as claimed.

What is claimed is:

1. An ultrasonic liquid jet probe for coupling transducer-emitted ultrasonic waves with a structure comprising:
   a housing disposed about said transducer, said transducer having an emitting/receiving end, and said housing comprising:
   (a) inlet means comprising at least two inlet ducts spaced symmetrically about said housing for receiving liquid under pressure from a source thereof;
   (b) first and second chambers defined in the interior of said housing and in fluid communication with each other through a plurality of circumferentially spaced conduits, said first chamber being arranged to receive said liquid from said inlet ducts, said conduits being disposed upstream of said emitting/receiving end of said transducer and being aligned parallel to said liquid jet column and elongated sufficiently and of sufficient number for imparting a substantially laminar flow to said liquid flowing from said first to said second chambers; and,
   (c) a nozzle configured for receiving said liquid flowing through said second chamber, shaping the flow of said liquid into a liquid jet column to be discharged from said nozzle and guiding said ultrasonic waves between said transducer and said liquid jet column, said nozzle being disposed sufficiently close to said emitting/receiving end of said transducer for providing an obstruction-free ultrasonic path between said emitting/receiving end of said transducer and said nozzle and enabling said ultrasonic waves emitted by said transducer to be guided to said liquid jet column by only said nozzle.

2. The probe of claim 1 wherein:
   (a) said first chamber is annular; and
   (b) said second chamber is disposed downstream of said first chamber and comprises an upstream annular chamber section and a downstream cylindrical chamber section, said annular chamber section surrounding said emitting/receiving end of said transducer.

3. The probe of claim 2 wherein said nozzle is removeable and said housing is configured for permitting said transducer to be replaceable through said second chamber, said housing including means for locking said transducer in place.

4. The probe of claim 2 wherein the radially inner boundary of said annular chamber section of said second chamber is defined by a tubular extension of said housing, the interior of said tubular extension being sized for receiving said emitting/receiving end of said transducer.

5. The probe of claim 4 wherein the outer surface of the downstream portion of said tubular extension is beveled radially inwardly for modifying the direction of flow of said liquid.

6. The probe of claim 4 further comprising a sleeve fabricated of a sound attenuating material disposed between said transducer and said tubular extension of said housing.

7. The probe of claim 4 wherein said housing includes a cavity radially inward of said annular first chamber aligned with the center of said interior of said tubular extension and sized and shaped for receiving a portion of said transducer.

8. The probe of claim 1 wherein said inlet ducts are aligned substantially normal to the alignment of said plurality of conduits.

* * * * *